(12) United States Patent
Thompson et al.

(10) Patent No.: US 11,547,591 B2
(45) Date of Patent: *Jan. 10, 2023

(54) ORTHOSIS FOR DEFORMITY CORRECTION

(71) Applicant: Green Sun Medical, LLC, Fort Collins, CO (US)

(72) Inventors: Matthew Thompson, Corte Madera, CA (US); Paul M. Thompson, Fort Collins, CO (US)

(73) Assignee: Green Sun Medical, LLC, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/406,999

(22) Filed: May 8, 2019

(65) Prior Publication Data

US 2019/0262160 A1 Aug. 29, 2019

Related U.S. Application Data

(63) Continuation of application No. 14/598,543, filed on Jan. 16, 2015, now Pat. No. 10,667,940.

(60) Provisional application No. 61/928,709, filed on Jan. 17, 2014.

(51) Int. Cl.
*A61F 5/00* (2006.01)
*A61F 5/02* (2006.01)

(52) U.S. Cl.
CPC ............... *A61F 5/024* (2013.01); *A61F 5/02* (2013.01)

(58) Field of Classification Search
CPC .. A61F 5/02; A61F 5/022; A61F 5/024; A61F 5/026; A61F 5/028; A61F 5/03; A61F 5/0553; A41D 13/05; A41D 13/0525; A41D 13/0531

USPC ........... 602/19, 5, 6, 62, 63; 128/96.1, 100.1
See application file for complete search history.

(56) References Cited

U.S. PATENT DOCUMENTS

| 757,140 | A | | 4/1904 | Edward |
| 970,781 | A | | 9/1910 | Joseph |
| 1,589,670 | A | * | 6/1926 | Vartia ..................... A61F 5/024 602/36 |

(Continued)

FOREIGN PATENT DOCUMENTS

| CN | 1349395 A | 5/2002 |
| CN | 200963211 Y | 10/2007 |

(Continued)

OTHER PUBLICATIONS

EP15736949 Extended European Search Report dated Feb. 12, 2018.

(Continued)

*Primary Examiner* — Adam Baker
(74) *Attorney, Agent, or Firm* — Wilson Sonsini Goodrich & Rosati (57) ABSTRACT

Disclosed are systems and methods of correction of spinal deformity that overcome current limitations by utilizing a dynamic, multi-segment torso orthosis that allows motion during wear. The disclosed embodiments utilize a series of elastically coupled segments that conform to the circumference of the torso of a patient. Adjustable elastic coupling mechanisms are utilized to create and alter forces and moments that are applied to the torso through the segments. These elastic coupling mechanisms also allow each circumferential segment to move relative to the other segments giving the brace dynamic capability.

19 Claims, 10 Drawing Sheets

(56) References Cited

U.S. PATENT DOCUMENTS

| | | | |
|---|---|---|---|
| 1,650,650 A | 11/1927 | Pieper | |
| 2,223,276 A | 11/1940 | Ward | |
| 2,687,129 A | 8/1954 | Talkish | |
| 2,835,247 A | 5/1958 | Stabholc | |
| 3,177,869 A | 4/1965 | Bartels | |
| 3,420,230 A | 1/1969 | Louis | |
| 3,926,182 A | 12/1975 | Stabholz | |
| 3,945,376 A | 3/1976 | Kuehnegger | |
| 4,230,101 A | 10/1980 | Gold | |
| 4,648,390 A | 3/1987 | Friddle | |
| 4,807,605 A | 2/1989 | Mattingly | |
| 5,012,798 A | 5/1991 | Graf et al. | |
| 5,103,811 A | 4/1992 | Crupi, Jr. | |
| 5,127,897 A | 7/1992 | Roller | |
| 5,213,094 A * | 5/1993 | Bonutti | A61F 5/0123 601/33 |
| 5,405,313 A | 4/1995 | Albin | |
| 5,449,338 A | 9/1995 | Trudell | |
| 5,503,621 A * | 4/1996 | Miller | A61F 5/022 2/44 |
| 5,586,561 A | 12/1996 | Archer, III | |
| 5,840,051 A | 11/1998 | Towsley | |
| 5,876,361 A * | 3/1999 | Harris | A61F 5/024 602/19 |
| 5,916,188 A | 6/1999 | Ousdal | |
| 6,280,405 B1 | 8/2001 | Broselid | |
| 6,605,052 B1 | 8/2003 | Cool et al. | |
| 6,676,617 B1 | 1/2004 | Miller | |
| 6,749,579 B1 * | 6/2004 | Schroder | A61F 5/028 2/467 |
| 7,654,973 B2 | 2/2010 | Firsov | |
| 7,766,850 B2 | 8/2010 | Simanovsky | |
| 7,967,767 B2 | 6/2011 | Ogilvie | |
| 8,066,653 B2 | 11/2011 | Seon | |
| 8,235,924 B2 | 8/2012 | Bachmann et al. | |
| 9,452,074 B2 | 9/2016 | Wynne et al. | |
| 9,522,077 B1 | 12/2016 | Johnson | |
| 9,572,705 B2 | 2/2017 | Ingimundarson et al. | |
| 2004/0073150 A1 | 4/2004 | Roballey | |
| 2005/0010150 A1 * | 1/2005 | Firsov | A61F 5/0102 602/19 |
| 2005/0043660 A1 | 2/2005 | Stark et al. | |
| 2005/0137510 A1 * | 6/2005 | Dauny | A61F 5/024 602/23 |
| 2006/0161085 A1 | 7/2006 | Wikenheiser et al. | |
| 2006/0287625 A1 | 12/2006 | Rauch | |
| 2007/0010768 A1 | 1/2007 | Simanovsky | |
| 2008/0021357 A1 | 1/2008 | Firsov | |
| 2008/0208089 A1 | 8/2008 | Newkirk | |
| 2008/0262402 A1 | 10/2008 | Ogilvie | |
| 2009/0054818 A1 | 2/2009 | Kaufman et al. | |
| 2011/0184325 A1 | 7/2011 | Behzadian et al. | |
| 2011/0295170 A1 | 12/2011 | Laranjeira et al. | |
| 2012/0157901 A1 | 6/2012 | Galante | |
| 2014/0012171 A1 | 1/2014 | Brown et al. | |
| 2015/0297387 A1 | 10/2015 | Thompson et al. | |
| 2015/0328035 A1 | 11/2015 | Idowu et al. | |
| 2016/0008206 A1 | 1/2016 | Devanaboyina | |
| 2017/0042717 A1 | 2/2017 | Agrawal et al. | |
| 2017/0196722 A1 | 7/2017 | Murdock | |
| 2019/0183668 A1 | 6/2019 | Thompson | |

FOREIGN PATENT DOCUMENTS

| | | |
|---|---|---|
| CN | 201337539 Y | 11/2009 |
| CN | 201930103 U | 8/2011 |
| CN | 102599999 A | 7/2012 |
| CN | 103892953 A | 7/2014 |
| CN | 104382678 A | 3/2015 |
| CN | 104983498 A | 10/2015 |
| CN | 106163461 A | 11/2016 |
| CN | 205696114 U | 11/2016 |
| CN | 107110485 A | 8/2017 |
| DE | 2743996 A1 | 4/1979 |
| EP | 1854435 A2 | 11/2007 |
| EP | 1983947 A1 | 10/2008 |
| ES | 2065289 A1 | 2/1995 |
| ES | 2264590 A1 | 1/2007 |
| FR | 2404430 A1 | 4/1979 |
| FR | 2591473 A1 | 6/1987 |
| GB | 190221246 A | 9/1903 |
| GB | 203975 A | 9/1923 |
| GB | 2215607 A | 9/1989 |
| JP | 2005137448 A | 6/2005 |
| JP | 2005349177 A | 12/2005 |
| JP | 2009119276 A | 6/2009 |
| JP | 2009148403 A | 7/2009 |
| KR | 20040103300 A | 12/2004 |
| KR | 20040103301 A | 12/2004 |
| RU | 2119312 C1 | 9/1998 |
| RU | 2131713 C1 | 6/1999 |
| TW | M280687 U | 11/2005 |
| WO | WO-02100304 A1 | 12/2002 |
| WO | WO-2005105004 A1 | 11/2005 |
| WO | WO-2012120316 A2 | 9/2012 |
| WO | WO-2015109174 A1 | 7/2015 |
| WO | WO-2019118789 A1 | 6/2019 |

OTHER PUBLICATIONS

International Search Report and Written Opinion dated Apr. 8, 2015 for International PCT Patent Application No. PCT/US2015/011741.
Office Action dated Jul. 7, 2017 for U.S. Appl. No. 14/598,543.
Office Action dated Dec. 8, 2016 for U.S. Appl. No. 14/598,543.
Final Office action dated Dec. 13, 2018 for U.S. Appl. No. 14/598,543.
U.S. Appl. No. 16/161,447 Office Action dated Oct. 5, 2021.
EP18888573.5 Extended Search Report dated Aug. 9, 2021.
Office action dated Mar. 30, 2021 for U.S. Appl. No. 16/161,447.
U.S. Appl. No. 14/598,543 Notice of Allowance dated Jan. 28, 2020.
International Preliminary Report on Patentability for PCT/US2018/06556 dated Jun. 16, 2020.
Office action dated Jun. 21, 2018 for U.S. Appl. No. 14/598,543.
Office action dated Aug. 6, 2019 for U.S. Appl. No. 14/598,543.

* cited by examiner

ORTHOSIS FOR DEFORMITY CORRECTION

CROSS REFERENCE TO RELATED APPLICATION

This application is a continuation of U.S. patent application Ser. No. 14/598,543, filed Jan. 16, 2015, which is based upon and claims the benefit of U.S. Provisional Application No. 61/928,709, filed Jan. 17, 2014, the entire disclosures of which are incorporated herein by reference.

BACKGROUND OF THE INVENTION

Adolescent Idiopathic Scoliosis (AIS) is an unnatural curvature of the spine that affects 2-3% of the population. Onset of this disease is typically around 10 years of age and is commonly detected (in the United States) in school screenings. The severity of the deformity is measured with the Cobb angle, the inside angle formed by the two most tilted vertebrae. The minimum Cobb angle for a diagnosis of IAS is 10 degrees. While many think of scoliosis as a curvature in the coronal plane, scoliosis can be a complex three-dimensional deformity often involving sagittal curves and rotational deformity in the axial plane.

The natural history of the disease is that many children will have curves of 10-20 degrees that remain static. Such an amount of curvature rarely requires treatment. The remainder of children with scoliosis have curves that continue to progress. Once the patient hits skeletal maturity, their curve will cease to progress if the Cobb angle measures less than 40 degrees. Curves with a Cobb angle of 40 degrees and greater, typically continue to progress.

Treatment for scoliosis is typically observational when curves are less than 25 degrees. Once curves reach 25 to 30 degrees of Cobb angle the patient is braced in an attempt to slow or halt progression of the curve. Curves that progress to 40 degrees or more are treated surgically with a spinal fusion.

Clinical studies have discovered two requirements for success in brace treatment: brace wear for 20 hours a day or more and acute correction of the scoliotic curve of at least 50% at brace application.

The current state of the art (standard of care) in bracing is a rigid full-torso brace known as a thoracolumbar-sacral orthosis (TLSO). This is typically a thermoplastic shell that is custom molded to the patient's torso with modifications that are intended to reduce the curvature through contact forces. These braces may have some effect in halting the progression of the curvature when worn comprehensively (often more than 20 hours per day) through the treatment period. Often these patients will be prescribed a brace for four or more years.

SUMMARY OF THE INVENTION

An embodiment of the present invention may therefore comprise: a system for externally applying corrective force to a vertebral column of a patient comprising: a plurality of ring segments that each conform to the circumference of the torso of a patient and are positioned in a spaced, substantially coaxial configuration about a vertical axis; one or more adjustable coupling mechanisms elastically coupled between adjacent ring segments comprising; at least one elastic member secured and adjustably fixated at a proximal end to a drive unit, the drive unit that is rigidly secured to the ring; at least one receiver rigidly mounted on an adjacent circumferential ring in a substantially coplanar arrangement that engages a distal end of each elastic member and allows limited axial and lateral motion while inhibiting transverse motion thereby translating a transverse or rotational force between the adjacent circumferential ring segments.

An embodiment of the present invention may also comprise: a system for externally applying corrective force to a vertebral column of a patient comprising: a plurality of ring segments that each conform to the circumference of the torso of a patient and positioned in a spaced, substantially coaxial configuration about a vertical axis; one or more dorsal adjustable coupling mechanisms elastically coupled between adjacent ring segments comprising; at least one elastic member secured and adjustably fixated at a proximal end to a dorsal drive unit, the dorsal drive unit that is rigidly secured to a dorsal portion of the ring segment; and, at least one dorsal receiver rigidly mounted to a dorsal portion of an adjacent circumferential ring in a substantially coplanar arrangement that engages a distal end of each elastic member and allows limited motion in a lateral and sagittal plane while inhibiting front-to-back motion in a transverse plane thereby translating a transverse or rotational force between the adjacent circumferential ring segments; a lateral adjustable coupling mechanism elastically coupled between adjacent ring segments comprising; at least one elastic member secured and adjustably fixated at a proximal end to a lateral drive unit, the lateral drive unit that is rigidly secured to a lateral portion of the ring segment; and, at least one lateral receiver rigidly mounted to a lateral portion of an adjacent said circumferential ring in a substantially coplanar arrangement that engages a distal end of each elastic member and allows limited motion in a sagittal and lateral plane while inhibiting side-to-side motion in a transverse plane thereby translating a transverse or rotational force between the adjacent circumferential ring segments.

An embodiment of the present invention may also comprise: a method of externally applying corrective force to a vertebral column of a patient comprising: placing a plurality of ring segments in a spaced, substantially coaxial configuration about a vertical axis on the torso of a patient such that each ring conforms to the circumference of the torso; securing and adjustably fixating a proximal end of at least one elastic member to a drive unit, the drive unit that is rigidly secured to the ring; coupling adjacent ring segments by engaging a distal end of each elastic member with at least one receiver that is rigidly mounted on an adjacent ring in a substantially coplanar arrangement; allowing limited axial and lateral motion between the adjacent rings; inhibiting transverse motion between the adjacent rings; and translating transverse or rotational force between the adjacent ring segments to facilitate a corrective force on the vertebral column of the patient.

DETAILED DESCRIPTION OF THE INVENTION

While this invention is susceptible to embodiment in many different forms, it is shown in the drawings, and will be described herein in detail, specific embodiments thereof with the understanding that the present disclosure is to be considered as an exemplification of the principles of the invention and is not to be limited to the specific embodiments described.

The rigid body braces mentioned above have many limitations. Reduction forces can be inconsistent or incorrect from ineffective brace forming, patient growth, changes in posture or insufficient strap tension. Currently there are no standard methods to adjust braces to provide the adequate reduction forces.

Using a conventional rigid brace, only acute correction can be achieved. Once tissue remodeling or growth occurs, the reduction forces immediately drop. In addition to questionable effectiveness of reduction (based upon clinical results), compliance is a major issue in brace treatment. Lack of compliance can come from pain, discomfort and cosmetic/lifestyle reasons. Many patients who are compliant, lose significant muscle tone from the lack of motion during the treatment period.

Figure 1:
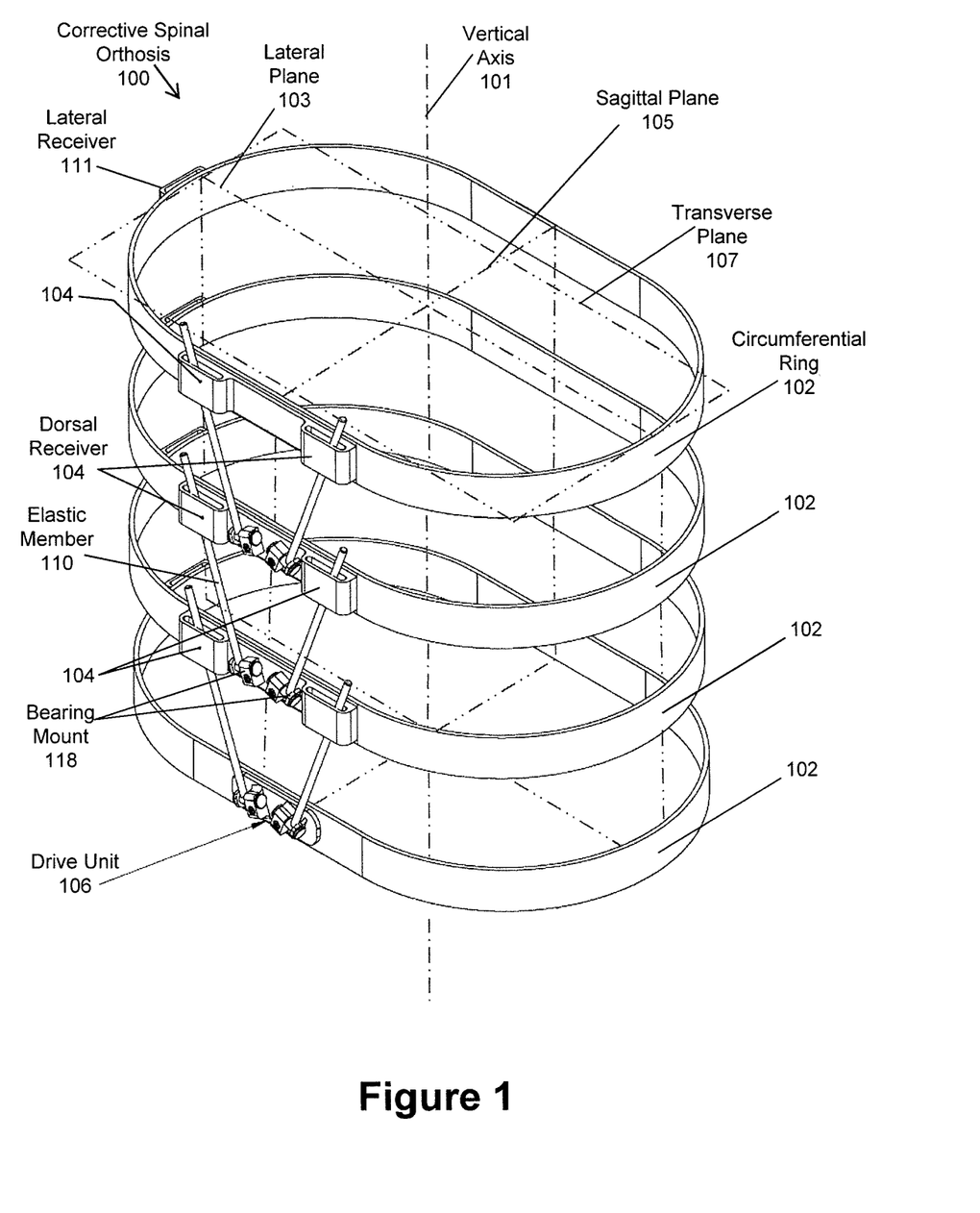
FIG. 1 illustrates an isometric view of an embodiment of an orthosis for correction of spinal deformity.
Figure 2:
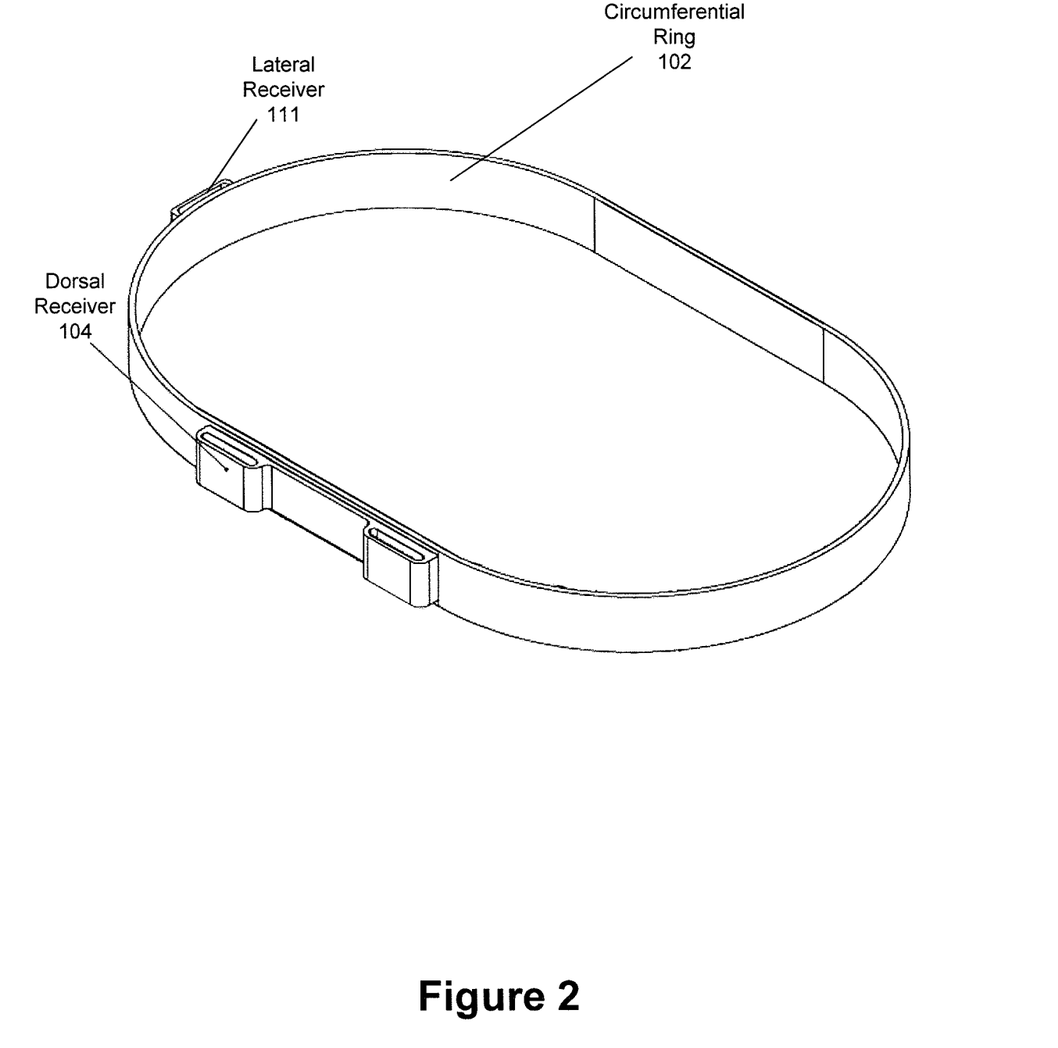
FIG. 2 illustrates an isometric view of an embodiment of a circumferential ring utilized in an orthosis for correction of spinal deformity.
Figure 3:
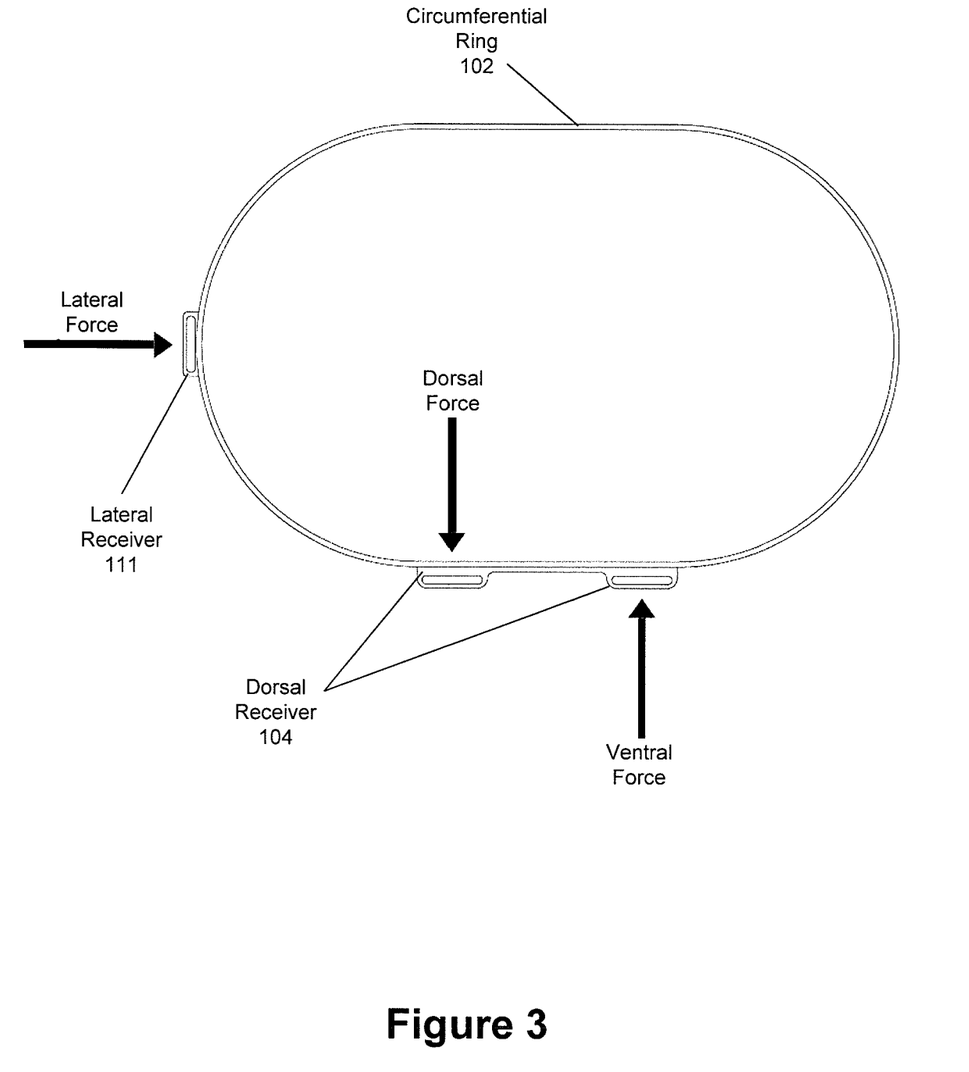
FIG. 3 illustrates a top plan view of an embodiment of a circumferential ring with receiver mechanisms utilized in an orthosis for correction of spinal deformity.

As shown in FIG. 1, an embodiment of an orthosis for correction of spinal deformity illustrates the disclosed system that overcomes the current limitations by utilizing a dynamic, multi-segment torso brace that allows motion during wear. Similar in theory to orthodontic methods, which utilize the application of forces to reposition teeth, the disclosed system exploits the physiological response of a body over time to constant force, called tissue remodeling. The disclosed embodiments illustrate a series of segments that conform to the circumference of the torso of a patient. Each of these segments is elastically coupled to an adjacent segment or segments. An adjustable elastic coupling mechanism is capable of creating and altering forces and moments that are applied to the torso through the segment. This elastic coupling mechanism also allows each circumferential segment to move relative to the other segments giving, the brace dynamic capability.

Figure 4:
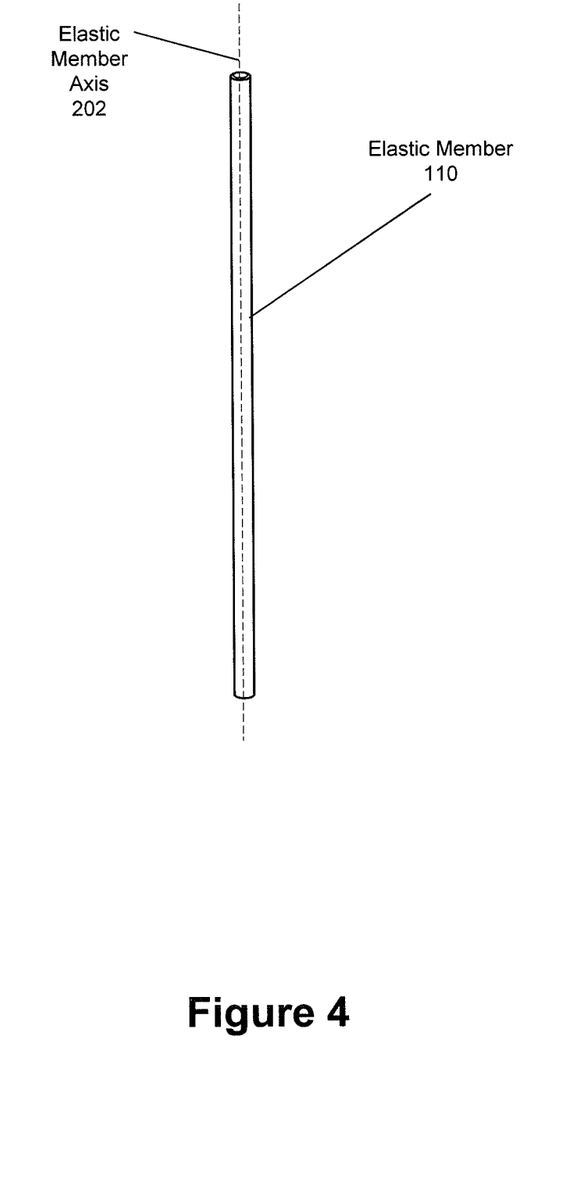
FIG. 4 illustrates an embodiment of an elastic member utilized in an orthosis for correction of spinal deformity.
Figure 5:
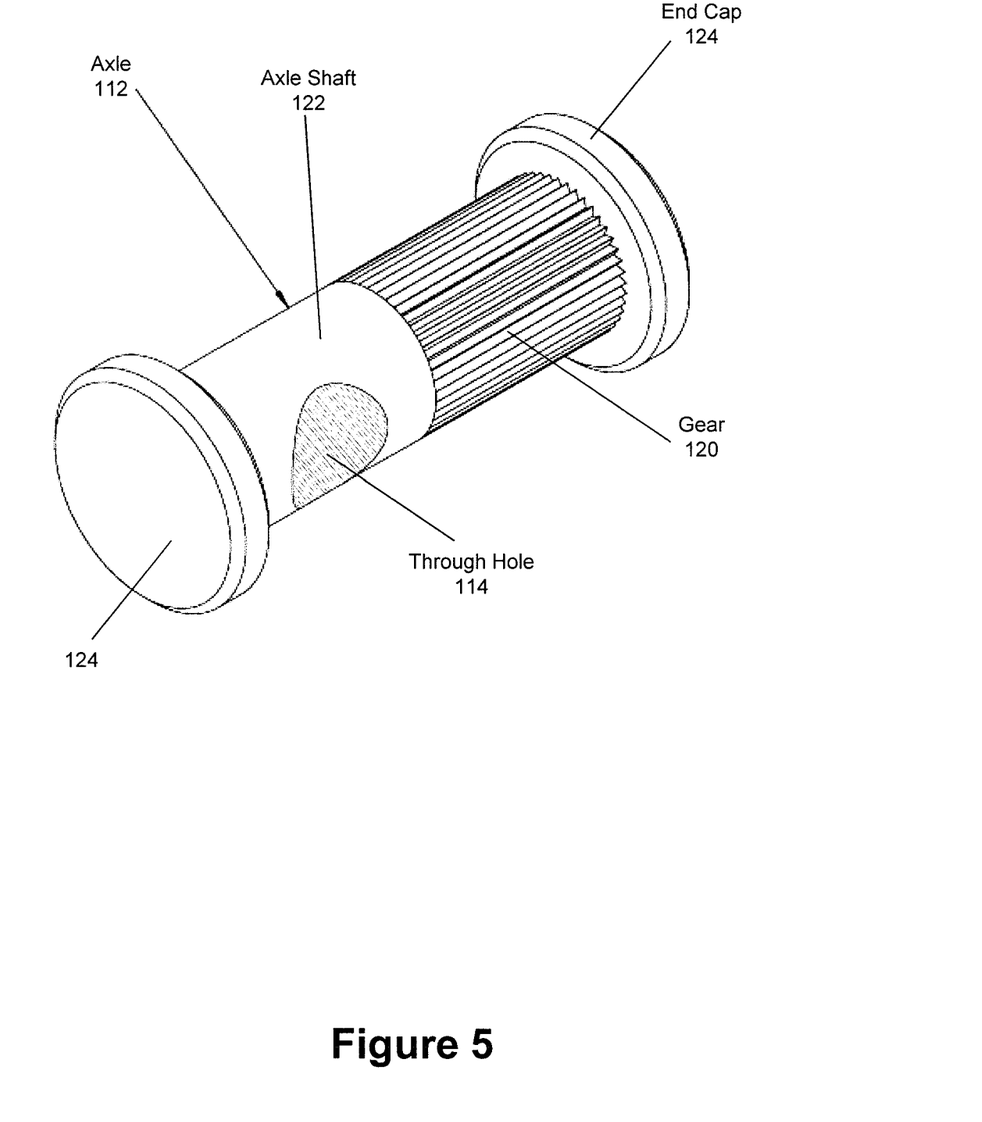
FIG. 5 illustrates an embodiment of an axle utilized in an orthosis for correction of spinal deformity.

The embodiment of FIG. 1 shows a series of interlinked circumferential rings 102. These circumferential rings 102 are typically a plurality of semi rigid bands that circumscribe the torso of the patient in the region from the sub-axillary thorax to the pelvis, superior of the greater trochanter. Each ring 102 is connected to at least one other ring in the plurality by at least one elastic member 110. Typically, a rod made of semi-rigid metal, polymer, graphite, carbon fiber, synthetic fiber, para-aramid synthetic fiber, Kevlar, fiberglass, or the like, or any combination thereof may be utilized. Materials utilizing shape memory and superelasticity (also called pseudoelasticity) such as nitinol or the like may also be utilized. In the embodiment disclosed on FIG. 1, a pair of elastic members 110, like the one shown in FIG. 4, physically communicates with each circumferential ring 102. In this embodiment, the inferior most circumferential ring 102 fixates the proximal (inferior) end of the pair of elastic members 110 on the dorsal portion of the ring utilizing retention hardware, which is in this circumstance, an axle 112. The axle 112, detailed in FIG. 5, contains a through-hole 114 that facilitates insertion and fixation of the elastic member 110, while maintaining a perpendicular (coincidental) orientation of the longitudinal axis of the axle 112 and the elastic member 110.

Figure 6:
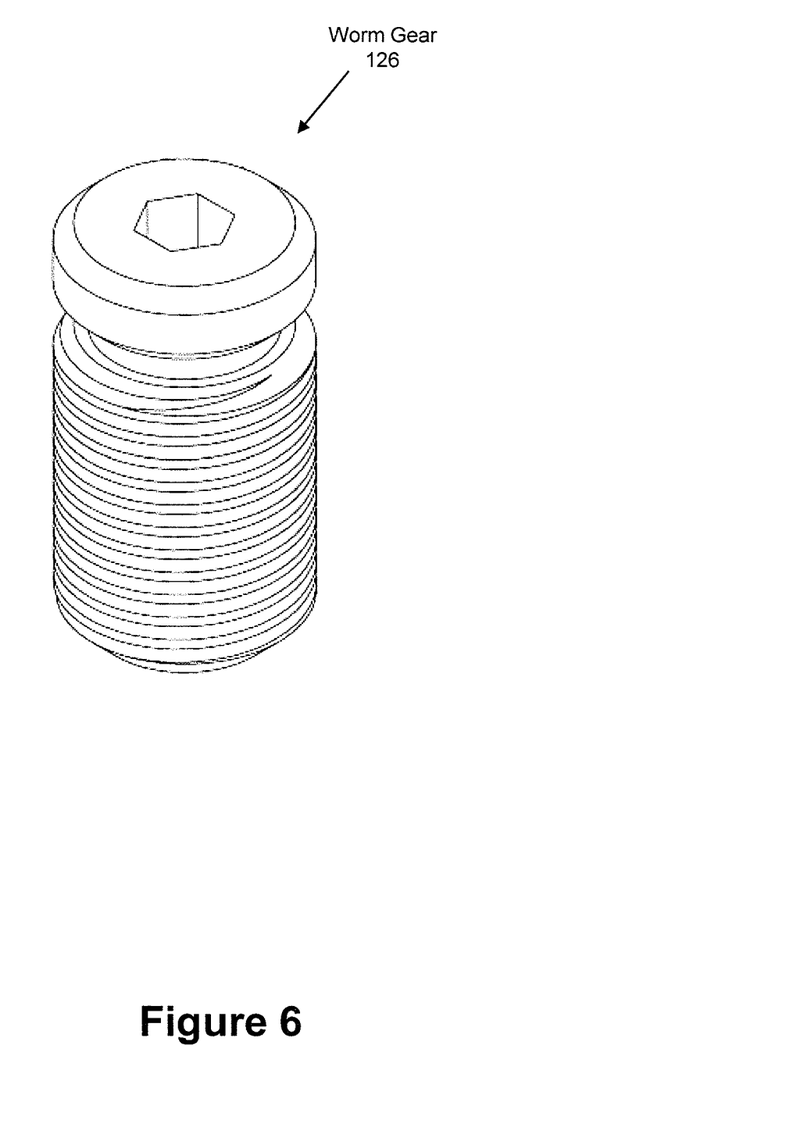
FIG. 6 illustrates an embodiment of a worm gear utilized in an orthosis for correction of spinal deformity.

The axle 112 is inserted into a drive unit 116 that contains fixed bearing mounts 118 for each axle 112. These bearing mounts 118 secure the position of the axle 112 while allowing a limited amount of rotation. The rotation and orientation of the axle 112 may be fixated and positioned within the bearing mount 118 utilizing a set of gears. In this example, the axle 112 contains a toothed portion (gear 120) on the outer surface of the axle shaft 124 that meshes with a worm gear 126 (see FIG. 6) mounted and fixated to rotate within a bearing mount 118. In this embodiment, the axle 112 is inserted between a pair of fixed bearing mounts 118 and held in place with endcaps 124 that fix the position of the axle 112 within mounts while allowing limited rotation. The rotation of the axle 112 is precisely fixated and positioned utilizing the worm gear 126 meshing with the axle shaft gear 120. Thus, rotation of the worm gear 126 produces an alteration of the axle 112 rotation, which produces a force tending to change the orientation of the fixated end of the elastic member 110.

The elastic member 110 extends to, and communicates with, the next adjacent circumferential ring 102 and is accepted by a receiver (in this example a dorsal receiver 104). The dorsal receiver 104 may comprise a constraining notch that restricts movement of the elastic member 110 in certain directions thereby transmitting force, while allowing motion in other directions, thereby allowing movement.

In the embodiment illustrated in FIG. 1, the opening in the dorsal receiver 104 that the elastic member 110 is inserted into is a semi-rectangular notch. This allows movement between the adjacent rings 102 in the longitudinal direction of the elastic member 110, while restricting motion in the lateral direction of the short side of the rectangular notch, and limiting the motion in the lateral direction of the long side of the rectangular notch (perpendicular to the short side).

Because of the complex 3-dimensional nature of spinal deformity, successful reduction of the curve relies upon a combination of forces and moments applied to the torso. Because of the need for de-rotation of the rib cage when axial deformity is present, each segment of the embodiments conforms to the circumference of the patient's torso without significant slippage or deformation. This rigid segment ensures that the system provides forces to counter the deformation rotation and provide the necessary reduction forces and moments. The illustration of FIG. 1, details the multi-segmented orthosis as a series of interlinked circumferential rings 102 that are positioned in a spaced, substantially coaxial configuration about a central vertical axis 101 extending centrally perpendicular to the rings 102, and typically oriented in the transverse plane 107 as shown.

Successful reduction of complex spinal deformity relies upon placing complex forces on the torso. The disclosed embodiment allows the circumferential rings 102 to be custom sized to a patient for a snug but comfortable fit. The individual sections of the spine may be manipulated by the force that the ring 102 places on the torso. As shown in FIG. 1, the inferior most circumferential ring 102 comprises a drive unit 106 that includes the proximal mounting and adjustment surfaces for the elastic members 110. These mechanisms, in combination with the receiver section (e.g., dorsal receiver 104 and/or lateral receiver 111), facilitate a transfer of force form orthotic section to section, and thus, spinal section to section.

Figure 7:
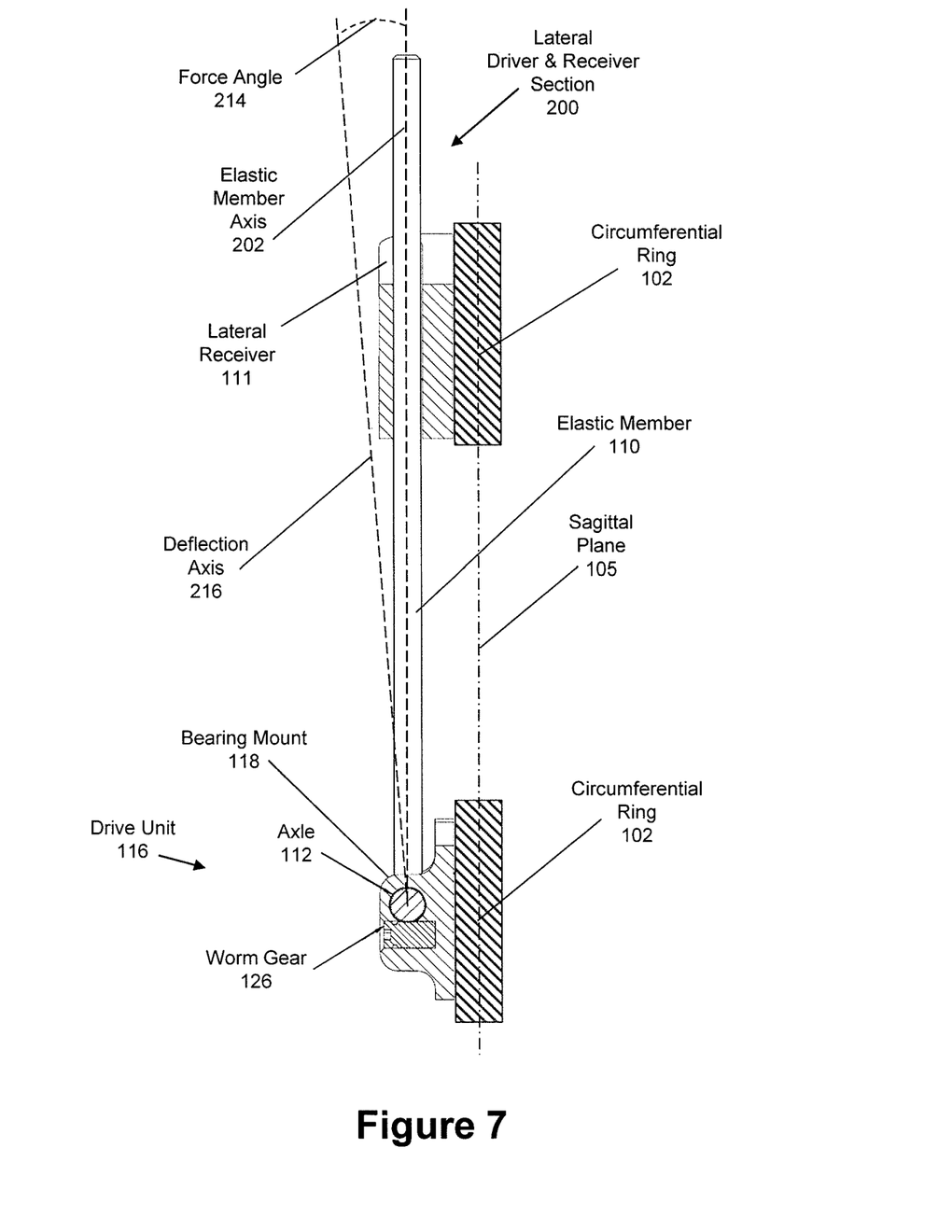
FIG. 7 illustrates a cross-sectional side view of an embodiment of a drive mechanism and receiver section utilized in an orthosis for correction of spinal deformity.
Figure 8:
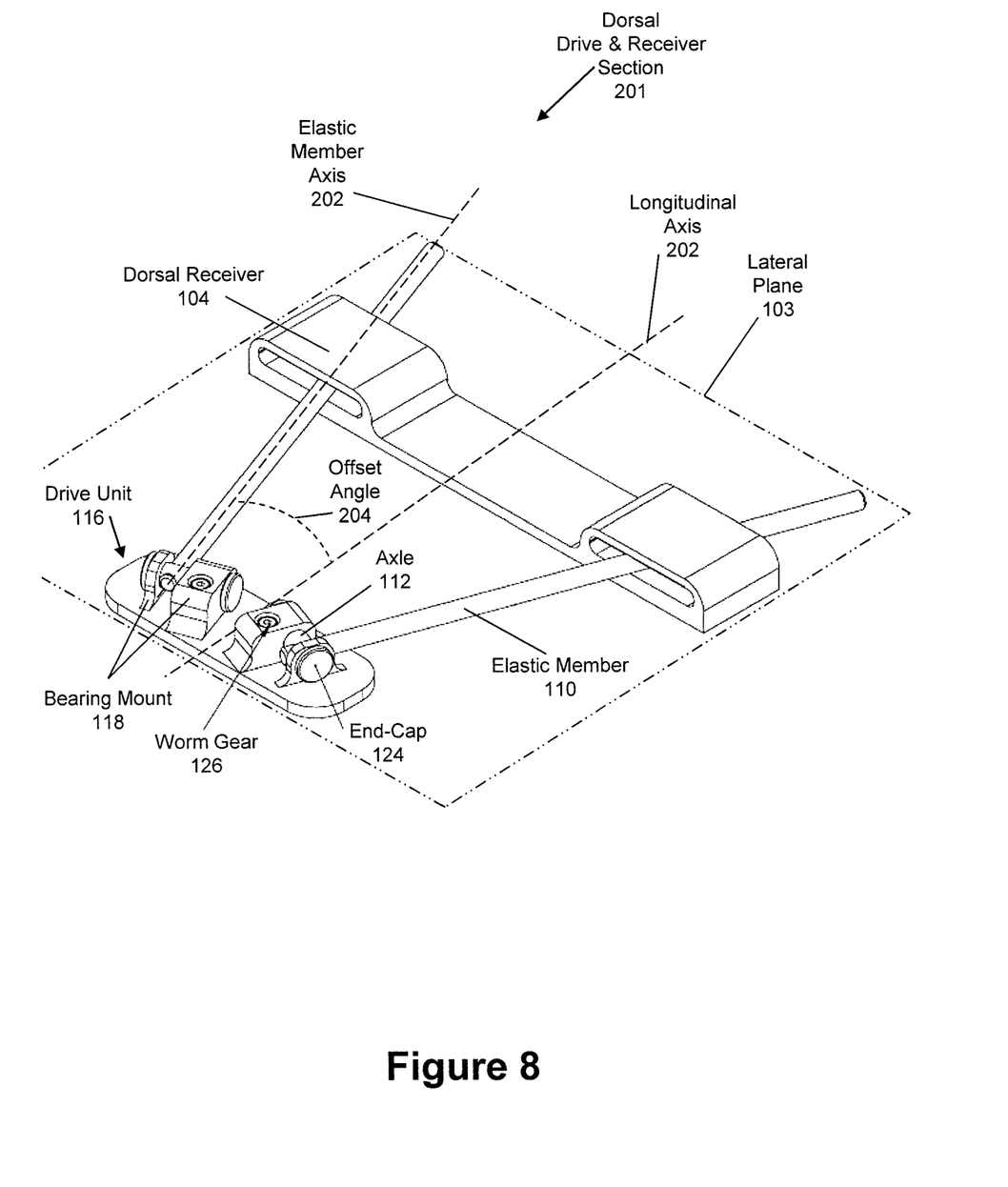
FIG. 8 illustrates an isometric view of an embodiment of an adjustable coupling mechanism on the form of a dual drive mechanism and receiver section utilized in an orthosis for correction of spinal deformity.
Figure 9:
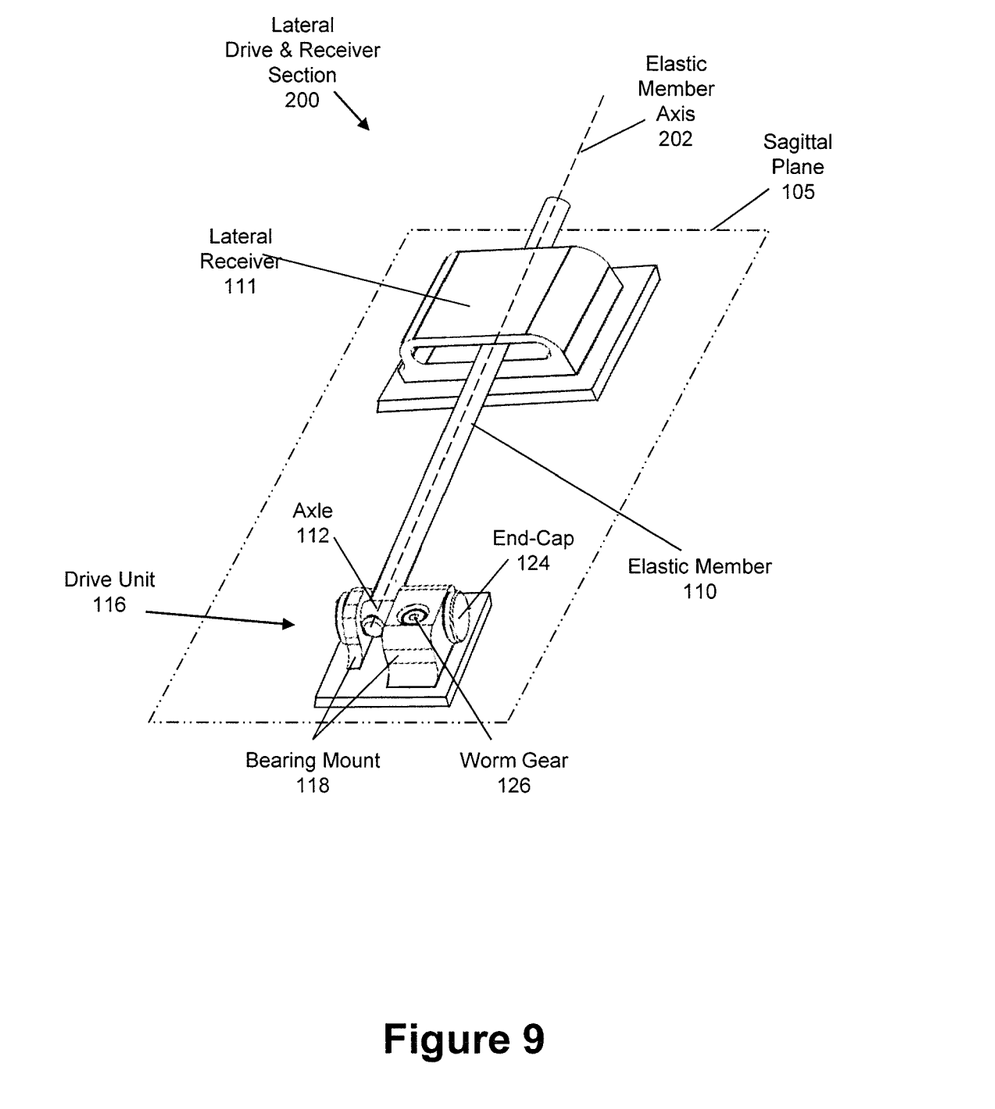
FIG. 9 illustrates an isometric view of an embodiment of an adjustable coupling mechanism on the form of a single drive mechanism and receiver section utilized in an orthosis for correction of spinal deformity.

As shown further in FIGS. 7-9, force may be communicated from the attached ring 102 to the bearing mounts 118 of the drive unit 116. The bearing mounts fixate the axle 112, which in turn fixates the elastic member. The force communicated between two adjacent ring 102 sections is adjusted in the sagittal plane 105 by setting the position angle of the two elastic members 110 and may facilitate a dorsal force communicated to the patient by pulling one ring away from the vertical axis 101 and lateral plane 103, as well as being able to facilitate a ventral force in the patient by pulling one ring towards the vertical axis 101 and lateral plane 103. Since this adjustable coupling mechanism communicating in a drive and receiver section 200 on the dorsal receiver 104 may be set to push on one side while the other pulls, anti-rotational forces may be applied between ring 102 segments.

Lateral adjustments may be facilitated utilizing another adjustable coupling mechanism in the form of a lateral receiver 111 that is utilized to apply force in the sagittal plane 105 of the wearer. These forces can also either push or pull the spine into proper alignment. When the lateral forces are combined with the dorsal and ventral forces (positive and/or negative), a system that allows a wide variety of therapeutic spinal forces is accomplished, including anti-rotation. Front-to-back (dorsal-ventral) and side-to-side (lateral and rotation) disorders may all be treated with a single customized, adjustable force orthosis. Complex maladies such as scoliosis (including de-rotation) may be treated and corrected utilizing the disclosed system as well as other (typically less complex) spinal disorders such as lordosis and kyphosis. These forces may be applied to the entire length of the movable spine or they may be segmented individually to the cervical, thoracic, or lumbar regions of the spine. By allowing the elastic members 110 to move in their axial direction within the receiver (104, 111), the wearer is afforded some movement and freedom in certain directions. The size and orientation of the receiver (104, 111) and the length and width of the receiving slot determine the amount of movement that the orthosis affords the wearer. This too is highly variable and customizable.

The adjustable coupling mechanism shown in FIG. 7 illustrates a side view of a single elastic member 110 mounted to a drive unit 116 utilizing sets of bearing mounts 118. The lateral receiver 111 is mounted on an adjacent circumferential ring 102 section in a substantially coplanar orientation about a sagittal plane 105. Where the drive unit 116 and lateral receiver 111 are shown coplanar, it is within the scope of the disclosure that variations in the anatomy of the wearer's torso may place the orientation in a substantially coplanar orientation due to spinal malcurvature, misalignment, disorder, trauma or other anatomical variation. By setting the position of the axle 112 utilizing, for instance, a worm gear mechanism, a push and/or pull of the elastic member 110 in the sagittal plane 105 is realized. The force angle 214 (in this example shown as a pull force wanting to create the deflection axis 216) facilitates a force that is precisely adjustable in magnitude and direction to perform a variety of corrective actions.

Figure 10:
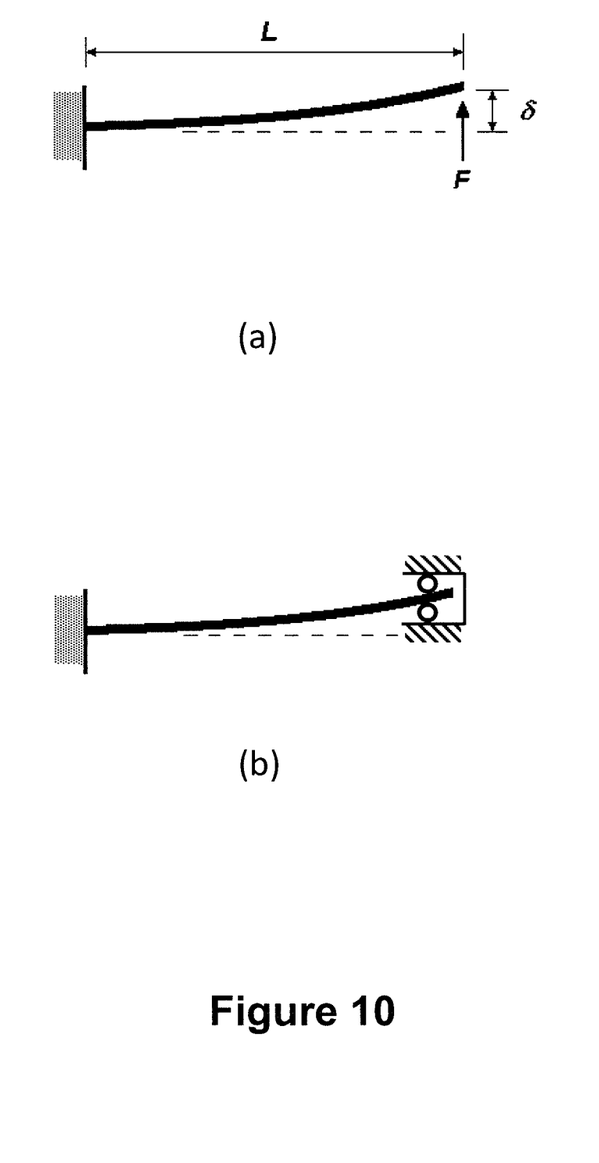
FIG. 10 is a diagram showing the physical principals of elastic deflection of a cantilever beam.

As illustrated in FIG. 7, it is apparent that the elastic member 110 is acting as a classic spring beam deflection model with a beam of length (L) is fixed at one end (by the drive unit 116) and is deflected by a force (F) by an amount (δ) (see FIG. 10 (a)), where the deflection $\delta = FL3//3EI$, and E is the Young's Modulus of the beam, and I is the moment of inertia of the beam. Utilizing these principals, the beam may be tailored to a patient's specific corrective need, in the sense that if more or less force is needed, or preferential forces need to be utilized to provide optimal correction, the beam properties may be easily changed. For example, a beam with a round cross-section may be utilized when no preferential forces are needed in the lateral or sagittal plane, but if the patient were in need of correction where preferential forces in either the lateral or sagittal plane would optimize their outcome, a rectangular (or other nonsymmetrical) shape may be utilized.

| Moment of inertia for round section | Moment of inertia for rectangular section |
|---|---|
| $I = \pi r^4/4 = \pi d^4/64$ where r and d are the radius and diameter respectively | $I = bh^3/12$ where h is the dimension in the plane of bending, i.e. in the axis in which the bending moment is applied |

In this example, by adjusting the height (h) and width (b) characteristics of the elastic member 110 (beam), the forces displaced from ring segment 102 to ring segment may be varied. Whereas, the above shows a spring beam depicted as a cantilever beam, the force F is actually translated to the adjacent ring segment 102 and acts more as a simply supported beam, for the beam is fixed at one end and simply supported at the other (see FIG. 10 (b)). This too is a simplification for demonstrative purposes, because the force produced by the coupling of the adjacent ring segments 102 is transmitted as a corrective force to the patient.

The adjustable coupling mechanism shown in FIG. 8 utilizes a pair of elastic members 110 mounted to a drive unit 116 utilizing sets of bearing mounts 118 offset from the longitudinal axis 202 by an offset angle 204. The dorsal receiver 104 is mounted on an adjacent ring 102 section (as depicted in FIG. 1 for example) in a substantially coplanar orientation about a lateral plane 103. Where the drive unit 116 and dorsal receiver 104 are shown coplanar, it is within the scope of the disclosure that variations in the anatomy of the wearer's torso may place the orientation in a substantially coplanar orientation due to spinal malcurvature, misalignment, disorder, trauma or other anatomical variation. By setting the position of the axle 112, a push and/or pull of the pair of elastic members 110 in the lateral plane 103 is realized. The offset angle 204 facilitates a force that is precisely adjustable in magnitude and direction to perform a variety of corrective actions.

The adjustable coupling mechanism shown in FIG. 9 illustrates an isometric view of the single lateral receiver 111 and elastic member 110 mounted to a drive unit 116 utilizing sets of bearing mounts 118. The dorsal receiver 104 is mounted on an adjacent ring 102 section (as depicted in FIG. 7 for example) in a substantially coplanar orientation about a sagittal plane 105.

Depending upon the type, degree and complexity of the mal-curvature of the spine, two or more rings 102 may be combined to customize an orthotic to resist and correct such disorders.

In an instance where the curvature disorder is small or localized, fewer ring segments may be necessary, and in a situation where the spine is significantly deformed, a large number of rings 102 may be utilized. The design also allows for smaller ring segments to be positioned beyond the torso extending to the head, leg, arm, shoulder or neck, if the need exists. With this high degree of variability, the orthosis may also have application as a mobility limiting splint to immobilize certain movements after surgery or trauma.

The Hooke's (spring force constant) or Young's Modulus of the elastic member 110 may also be varied to provide additional restraint or flexibility between the circumferential rings 102. In a situation where a small adolescent patient needs correction, a more flexible rod may be beneficial, whereas a stiffer elastic member 110 may be utilized for a larger, heavier adult patient or in a situation where greater immobilization is warranted. Various combinations of stiffness within the elastic members 110 may be combined to tailor an orthotic to an individual patient for the intended outcome. This variability in stiffness may be implemented from ring section to ring section, or even within the individual drive and receiver sections 200, thereby providing yet additional customization for the wearer.

With the wide variability the system affords, precise forces may be placed upon the spine of the wearer. As the body responds to these forces, tissue remodeling and/or growth occur and these forces immediately drop. The disclosed system allows for easy readjustment of the applied forces to correct and re-align the spinal column and exploits the physiological response of a body over time to constant force. The patient may be initially evaluated and measured, the corrective geometry determined, and a custom orthosis may be created to precisely fit the body and corrective/stabilization needs of the wearer. With the ease of adjustment of the forces that the orthosis applies, the wearer may be refitted or adjusted on a routine, even short term basis such as weekly, bi-weekly or monthly depending upon the spinal response.

Successful reduction of complex spinal deformity also relies on using fixed reference endpoints that are not affected by deformity. In one embodiment of the disclosed orthotic system, the shoulders and pelvic girdle may serve as these reference endpoints.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A system for externally applying corrective forces to a vertebral column of a patient having a torso with a front, a back, and two sides, said system comprising:
   an inferior terminal ring segment;
   a superior terminal ring segment;
   at least one intermediate ring segment disposed between the inferior terminal ring segment and the superior terminal ring segment;
   wherein each ring segment has a front, a back, and two sides which are configured to fully circumscribe the front, the back, and the two sides of the torso of the patient;
   first adjustable coupling mechanisms mounted on a back surface of one of the two terminal ring segments and of each intermediate ring segment;
   second adjustable coupling mechanisms mounted on the back surface of the one terminal ring segment and of each intermediate ring segment;
   a first dorsal receiver mounted on a back surface of the other of the two terminal ring segments and of each intermediate ring segment;
   a second dorsal receiver mounted on the back surface of the other terminal ring segment and of each intermediate ring segment;
   a first elastic member attached to each of the first adjustable coupling mechanisms and extending to the first dorsal receiver on a vertically adjacent ring segment; and
   a second elastic member attached to each of the second adjustable coupling mechanisms and extending to the second dorsal receiver on the vertically adjacent ring segment;
   wherein the ring segments are separate from each other and are spaced-apart along a vertical axis and wherein each adjustable coupling mechanism is configured to rotate and to fixate an end of the attached elastic member so that the elastic member applies a force to the dorsal receiver on the adjacent ring segment, wherein the force rotates the adjacent ring about the vertical axis.

2. The system of claim 1, further comprising third adjustable coupling mechanisms positioned on a lateral surface of one of the two terminal ring segment and on each intermediate ring segments and is configured to rotate and fixate an end of an attached elastic member to deflect an axis of the attached elastic member to apply a force on a lateral receiver on an adjacent ring segment in a sagittal plane.

3. The system of claim 2, wherein each coupling mechanism comprises:
   a bearing mount;
   an axle secured on opposing ends to the bearing mount; and
   an adjustable fixator that allows said axle to be rotated for adjustment and fixated at a specific position thereby allowing a fixed positioning of said elastic member with respect to the coupling mechanism;
   wherein the attached end of said elastic member is connected to the axle such that the elastic member is oriented perpendicularly to a longitudinal axis of the axle.

4. The system of claim 1, wherein each elastic member comprises a spring beam.

5. The system of claim 1, wherein each elastic member comprises material chosen from the group consisting of a semi-rigid metal, a superelastic metal, a shape memory alloy, a polymer, a graphite, a synthetic fiber, a para-aramid synthetic fiber, a carbon fiber, fiberglass, and nitinol.

6. The system of claim 1, wherein the first and second adjustable coupling mechanisms are laterally spaced from each other on opposite sides of a longitudinal axis.

7. The system of claim 1, wherein the first and second adjustable coupling mechanisms are positioned closer to a longitudinal axis than are the first and second dorsal receivers such that said elastic members laterally diverge in a direction from the first and second adjustable coupling mechanisms toward the first and second dorsal receivers.

8. The system of claim 7, wherein the first and second dorsal receivers are laterally spaced from each other on opposite sides of a longitudinal axis.

9. The system of claim 7, wherein each dorsal receiver comprises a slot sized to allow a free end of the elastic member limited motion in a lateral and sagittal plane while inhibiting front-to-back motion in a transverse plane.

10. A method for externally applying corrective forces to a vertebral column of a patient having a torso with a front, a back, and two sides comprising:
   placing an inferior terminal ring segment about a circumference of a lumbar region of the patient's torso, wherein said inferior terminal ring segment has a front, a back, and two sides which fully circumscribe the front, the back, and the two sides of the patient's torso in the lumbar region;
   placing a superior terminal ring segment about a circumference of a cervical region of the patient's torso, wherein said superior terminal ring segment has a front, a back, and two sides which fully circumscribe the front, the back, and the two sides of the patient's torso in the cervical region;
   placing at least one intermediate ring segment about a circumference of the patient's thoracic region of the patient's torso, wherein said intermediate ring segment has a front, a back, and two sides which fully circumscribe the front, the back, and the two sides of the patient's torso in the thoracic region;
   wherein the ring segments are separate from each other and are spaced-apart along a vertical axis;
   securing first and second terminal elastic members between one of the terminal ring segments and a first intermediate ring segment;
   securing first and second intermediate elastic members between a first intermediate ring segment and the other of terminal ring segments; and
   rotating and fixating an end of each of the attached elastic members so that an opposite end the elastic member applies a force to the adjacent ring segment, wherein the force rotates the adjacent ring about the vertical axis.

11. A method as in claim 10, wherein rotating and fixating comprises adjusting (1) a first adjustable coupling mechanism mounted on a back surface of the terminal ring segment, (2) a second adjustable coupling mechanism mounted on the back surface of the terminal ring segment, (3) a first adjustable coupling mechanism mounted on a back surface of the intermediate ring segment, and a second adjustable coupling mechanism mounted on the back surface of the first intermediate ring segment.

12. A method as in claim 11, wherein the first and second adjustable coupling mechanisms apply a rotational force to an end of the elastic member to deflect an axis of the elastic member to apply a force in a lateral plane on a vertically adjacent ring segment.

13. A method as in claim 12, further comprising rotating and fixating a third adjustable coupling mechanism positioned on a lateral surface of one of the two terminal ring segment and on each intermediate ring segments wherein the third adjustable coupling mechanism applies a rotational force to an end of the elastic member to deflect an axis of the elastic member to apply a force in a sagittal plane on a vertically adjacent ring segment.

14. A method as in claim 11, wherein each coupling mechanism comprises:
   a bearing mount;
   an axle secured on opposing ends to the bearing mount; and
   an adjustable fixator that allows said axle to be rotated for adjustment and fixated at a specific position thereby allowing a fixed positioning of said elastic member with respect to the coupling mechanism;
   wherein the attached end of said elastic member is connected to the axle such that the elastic member is oriented perpendicularly to a longitudinal axis of the axle.

15. A method as in claim 11, wherein the first and second adjustable coupling mechanisms on the back surface of the terminal ring segment are laterally spaced from each other on opposite sides of a longitudinal axis and wherein the first and second adjustable coupling mechanisms on the back surface of the intermediate ring segment are laterally spaced from each other on opposite sides of the longitudinal axis.

16. A method as in claim 15, wherein the opposite ends of the elastic members are laterally spaced from each other on opposite sides of a longitudinal axis.

17. A method as in claim 16, wherein the first and second adjustable coupling mechanisms are positioned closer to the longitudinal axis than are the opposite ends of the elastic members such that said elastic members laterally diverge in a direction from the first and second adjustable coupling mechanisms toward the first and said opposite ends.

18. A method as in claim 17, wherein each opposite end of the elastic members is received in a slot sized to allow said opposite of the elastic member limited motion in a lateral and sagittal plane while inhibiting front-to-back motion in a transverse plane.

19. A method as in claim 10, wherein each elastic member comprises a spring beam.

* * * * *